(12) United States Patent
Jie et al.

(10) Patent No.: US 12,390,300 B2
(45) Date of Patent: Aug. 19, 2025

(54) TRADITIONAL CHINESE MEDICINE INSPECTION DEVICE OF COMPOSITE MILLIMETER-WAVE RADAR

(71) Applicant: Institute of Information on Traditional Chinese Medicine, China Academy of Chinese Medical Sciences, Beijing (CN)

(72) Inventors: Yang Jie, Beijing (CN); Liu Baoyan, Beijing (CN); Wang Bin, Beijing (CN); Wen Tiancai, Beijing (CN); Zhang Lei, Beijing (CN); Liu Jia, Beijing (CN)

(73) Assignee: Institute of Information on Traditional Chinese Medicine, China Academy of Chinese Medical Sciences., Beijing (CN)

( * ) Notice: Subject to any disclaimer, the term of this patent is extended or adjusted under 35 U.S.C. 154(b) by 302 days.

(21) Appl. No.: 18/136,890

(22) Filed: Apr. 20, 2023

(65) Prior Publication Data
US 2023/0338109 A1    Oct. 26, 2023

(30) Foreign Application Priority Data
Apr. 24, 2022  (CN) .......................... 202210432549.2

(51) Int. Cl.
*A61B 90/11*   (2016.01)
*A61B 5/00*    (2006.01)
(Continued)

(52) U.S. Cl.
CPC ................. *A61B 90/11* (2016.02); *A61B 5/00* (2013.01); *A61B 50/20* (2016.02); *A61B 90/50* (2016.02); *F16M 2200/068* (2013.01)

(58) Field of Classification Search
CPC ......... A61B 90/11; A61B 5/00; A61B 5/0205; A61B 1/042; A61B 1/04; A61B 50/24;
(Continued)

(56) References Cited

U.S. PATENT DOCUMENTS

| 2,518,288 A | * | 8/1950 | Coutant | ................. | F16M 11/42 |
| | | | | | 280/47.11 |
| 2,661,672 A | * | 12/1953 | Fairbanks | .............. | F16M 11/42 |
| | | | | | 280/47.11 |

(Continued)

*Primary Examiner* — Devin K Barnett
(74) *Attorney, Agent, or Firm* — Jose Cherson Weissbrot (57) ABSTRACT

The present disclosure provides a Traditional Chinese Medicine inspection device of a composite millimeter-wave radar, and relates to the technical field of Traditional Chinese Medicine detection devices. The Traditional Chinese Medicine inspection device of the composite millimeter-wave radar includes a base, wherein a moving frame is threadedly installed at the top end of the base, a mounting table is slidably installed at the top end of the moving frame, a driving device is installed inside the mounting table, and a connecting frame is rotatably installed at the top end of the mounting table; the driving device has a driving motor and a driving rod, a detection device is rotatably installed at the right end of a connecting arm body, and a transmission device is installed at the bottom end of the connecting arm body.

10 Claims, 6 Drawing Sheets

(51) Int. Cl.
*A61B 50/20* (2016.01)
*A61B 90/50* (2016.01)

(58) Field of Classification Search
CPC ......... A61B 50/20; A61B 90/35; A61B 90/50; F16M 2200/068; F16M 2200/08; F16M 2200/041; F16M 11/242; F16M 11/18; F16M 11/28; F16M 11/42; F16M 13/04
See application file for complete search history.

(56) References Cited

U.S. PATENT DOCUMENTS

| | | | | |
|---|---|---|---|---|
| 4,657,267 | A * | 4/1987 | Jaumann | F16M 11/42 396/419 |
| D361,587 | S * | 8/1995 | Chapman | D16/242 |
| 5,730,450 | A * | 3/1998 | Chapman | F16M 11/42 280/47.11 |
| 6,439,515 | B1 * | 8/2002 | Powers | F16M 13/04 248/129 |
| 6,443,543 | B1 * | 9/2002 | Chiang | A47B 21/00 312/319.7 |
| 8,142,083 | B2 * | 3/2012 | Brown | F16M 11/2035 396/421 |
| 8,205,841 | B2 * | 6/2012 | Wood | F16M 11/08 248/128 |
| 8,248,468 | B2 * | 8/2012 | Song | G01B 11/24 248/689 |
| D670,752 | S * | 11/2012 | Barber | D16/244 |
| 10,858,134 | B2 * | 12/2020 | Amano | B65H 23/044 |
| 11,666,412 | B2 * | 6/2023 | Pichler | A61B 90/50 211/85.13 |
| 12,194,645 | B1 * | 1/2025 | Telem | B25J 9/1669 |
| 2007/0296816 | A1 * | 12/2007 | Rubio | H04N 7/181 348/E7.086 |
| 2009/0315288 | A1 * | 12/2009 | Hernandez | F16M 11/06 280/79.3 |
| 2013/0342676 | A1 * | 12/2013 | Amano | G07F 9/026 348/86 |
| 2015/0196192 | A1 * | 7/2015 | Kan | F16M 11/42 211/85.13 |
| 2015/0327936 | A1 * | 11/2015 | Coleman | A47B 81/00 211/85.13 |
| 2019/0185182 | A1 * | 6/2019 | Bei | F16M 11/10 |
| 2020/0068105 | A1 * | 2/2020 | Telem | H04N 1/00289 |
| 2023/0065062 | A1 * | 3/2023 | Leblanc | F16M 11/20 |
| 2023/0181021 | A1 * | 6/2023 | Saltzburg | A61B 1/00016 348/66 |
| 2023/0240793 | A1 * | 8/2023 | Soto | A61B 34/30 211/85.13 |
| 2023/0415331 | A1 * | 12/2023 | Larsson | B25J 5/007 |
| 2024/0029237 | A1 * | 1/2024 | Rozeboom | G01N 21/8851 |
| 2024/0272270 | A1 * | 8/2024 | Longman | G01S 13/343 |
| 2024/0406415 | A1 * | 12/2024 | Amini | G08B 29/188 |
| 2025/0108254 | A1 * | 4/2025 | Tuxen | G01S 17/86 |

\* cited by examiner

TRADITIONAL CHINESE MEDICINE INSPECTION DEVICE OF COMPOSITE MILLIMETER-WAVE RADAR

CROSS REFERENCE

This application is based upon and claims priority benefits to Chinese Patent Application No. 202210432549.2, filed on Apr. 24, 2022, the contents of which are incorporated herein by reference.

TECHNICAL FIELD

The present disclosure relates to the technical field of Traditional Chinese Medicine detection devices, in particular to a Traditional Chinese Medicine inspection device of a composite millimeter-wave radar.

BACKGROUND

The information sources of Traditional Chinese Medicine diagnosis in China are mainly inspecting, listening, questioning and feeling, also referred to as "four diagnoses", in which inspecting mainly includes tongue diagnosis and face-to-face diagnosis, etc. The traditional inspection information collection mainly depends on subjective qualitative observation and clinical experience of a doctor.

However, as far as the current Traditional Chinese Medicine inspection device is concerned, the adjustable performance of the device is not good. It is not easy to adjust the height of the head supporting plate and the detection device of the device as required. It is not easy for a user to adjust the protruding position of the head supporting plate on the mounting table as required, and it is not easy to adjust the radius of the rotating arm of the detection device. The device can only shoot, upload and detect the face of a patient at a unidirectional angle, which is easy to affect the detection effect of the device. The staying positions of a user are different. It is not easy for a millimeter-wave radar to rotate according to the position of the human body, so as to detect the physical characteristics of the user such as the respiratory frequency and the heartbeat frequency at intervals.

SUMMARY

In view of this, the present disclosure provides a Traditional Chinese Medicine inspection device of a composite millimeter-wave radar, which is provided with a clamping block. The bottom end of the clamping block is in a symmetrical italic structure with a narrow upper part and a wide lower part, so that the clamping block can be clamped and installed on the clamping groove on the top surface of the connecting frame. At the same time, it is convenient for the clamping block to move up and down, thereby facilitating the position adjustment of the connecting frame.

The present disclosure provides a Traditional Chinese Medicine inspection device of a composite millimeter-wave radar, which specifically comprises a base;

wherein an adjusting screw is rotatably installed at the left end of the base, a universal wheel is provided at the bottom end of the base, a moving frame is threadedly installed at the top end of the base, a limit plate is provided at the outer side of the top end of the moving frame, a processor is installed at the rear end of the top surface of the moving frame, a remote transmission module is provided in the processor, a database is provided in the processor, a mounting table is slidably installed at the top end of the moving frame, a head supporting plate is provided at the top end of the front side of the mounting table, a driving device is installed inside the mounting table, and a connecting frame is rotatably installed at the top end of the mounting table; the driving device comprises a driving motor and a driving rod, the driving motor is fixedly installed at the inner bottom end of the mounting table, the driving rod is fixedly installed at the left end of the connecting frame, and the driving rod is rotatably installed on the mounting table; a connecting arm body is installed at the right end of the connecting frame; a clamping block is slidably installed at the left bottom end of the connecting arm body, the clamping block is clamped and installed at the top end of the connecting frame, a detection device is rotatably installed at the right end of the connecting arm body, a transmission device is installed at the bottom end of the connecting arm body, the detection device comprises a supporting rod, a camera, a millimeter-wave radar and a rotating rod, the camera is installed at the middle section of the supporting rod, the millimeter-wave radar is installed at the top end of the supporting rod, and the rotating rod is provided at the bottom end of the supporting rod; the transmission device comprises a transmission motor, a pinion and a large gear, the transmission motor is fixedly installed at the right bottom end of the connecting arm body, and the pinion is installed on a transmission shaft of the transmission motor.

Preferably, either end of the clamping block slidably installed at the bottom end of the connecting arm body is provided with a sliding hole, respectively, two sliding rods are fixedly installed on the left bottom surface of the connecting arm body, a limit post is provided at the bottom end of the sliding rod, and the sliding holes at both ends of the clamping block at the bottom end of the connecting arm body are slidably installed on the sliding rod fixedly installed on the left bottom surface of the connecting arm body, respectively.

Preferably, an adjusting motor is fixedly installed at the left end of the base, the bottom end of the adjusting screw is installed on the transmission shaft of the adjusting motor, a threaded hole is provided at the left end of the bottom plate at the bottom end of the moving frame, and the threaded hole on the bottom plate at the bottom end of the moving frame is threadedly installed on the adjusting screw rotatably installed at the left end of the base.

Preferably, the top surface of the connecting frame is provided with clamping grooves at equal intervals in an array, the bottom end of the clamping block installed on the connecting arm body is in a symmetrical italic structure with a narrow upper part and a wide lower part, and the clamping block on the connecting arm body is clamped and installed on the clamping grooves on the top surface of the connecting frame.

Preferably, an elastic element is sleeved and installed to either of the two sliding rods on the left bottom surface of the connecting arm body, respectively, and the bottom end of the elastic element is in contact with the top end of the clamping block.

Preferably, two external sliders are provided at the left side and the right side of the mounting table, respectively, a guide rail is provided at the top end of the moving frame, and the external sliders at the left side and the right side of the mounting table are slidably installed on the guide rail provided at the top end of the moving frame.

Preferably, the driving device further comprises an incomplete bevel gear, an upper bevel gear and a lower bevel gear, the incomplete bevel gear is installed on the transmission shaft of the driving motor, the upper bevel gear and the lower bevel gear are installed on the driving rod oppositely, and the upper bevel gear and the lower bevel gear are in meshing transmission connection with the incomplete bevel gear, respectively.

Preferably, a guide groove is provided at the top end of the connecting arm body, and the right end of the connecting frame is slidably installed on the guide groove provided at the top end of the connecting arm body.

Preferably, a guide rod is fixedly installed at the right end of the base, a bottom plate is provided at the bottom end of the moving frame, a guide hole is provided at the right end of the bottom plate, and the guide hole on the bottom plate at the bottom end of the moving frame is slidably installed on the guide rod fixedly installed at the right end of the base.

Preferably, the rotating rod on the detection device is rotatably installed at the right end of the connecting arm body, the large gear is fixedly installed at the bottom end of the rotating rod on the detection device, and the pinion is in meshing transmission connection with the large gear at the bottom end of the rotating rod.

Beneficial Effects

Compared with the past Traditional Chinese Medicine inspection device, for the Traditional Chinese Medicine inspection device according to each embodiment of the present disclosure, the head supporting plate and the detection device of the Traditional Chinese Medicine inspection device can be adjusted in height as required. A user can adjust the protruding position of the head supporting plate on the mounting table as required, and it is convenient to adjust the radius of the rotating arm of the detection device, so that the adjustable performance of the device is improved. The detection device of the Traditional Chinese Medicine inspection device rotates around the head of the user for half a turn for reciprocating motion, and cooperates with the camera and the millimeter-wave radar on the detection device, so that the camera can shoot and upload the face of a patient from different angles and carry out comparative detection through the processor, which improves the detection effect of the device on face-to-face diagnosis of the user. The camera is cooperated with the processor, and the detection device of the device can be controlled to rotate according to the position of the user, so that the millimeter-wave radar can detect the physical characteristics of the user such as the respiratory frequency and the heartbeat frequency at intervals.

In addition, the guide hole on the bottom plate at the bottom end of the moving frame is slidably installed on the guide rod fixedly installed at the right end of the base. The threaded hole on the bottom plate at the bottom end of the moving frame is threadedly installed on the adjusting screw rotatably installed at the left end of the base. The adjusting motor drives the adjusting screw to rotate, so that the moving frame threadedly installed on the adjusting screw and the head supporting plate and the detecting device thereon can be adjusted in height as required.

In addition, the external sliders at the left side and the right side of the mounting table are slidably installed on the guide rail provided at the top end of the moving frame, so that the user can conveniently adjust the protruding position of the head supporting plate on the mounting table as required. The right end of the connecting frame is slidably installed on the guide groove provided at the top end of the connecting arm body. The sliding holes at the both ends of the clamping block at the bottom end of the connecting arm body are slidably installed on the sliding rod fixedly installed on the left bottom surface of the connecting arm body, respectively. In cooperation with the elastic element sleeved and installed on the sliding rod, the connecting frame is pulled outwards, so that the clamping block on the connecting arm body is clamped and installed on different clamping grooves on the top surface of the connecting frame. In this way, it is convenient to adjust the radius of the rotating arm of the detection device, so that the adjustable performance of the device is improved.

In addition, the user sticks his chin on the head supporting plate, so that the driving motor drives the incomplete bevel gear to rotate. When the incomplete bevel gear is in meshing transmission connection with the upper bevel gear on the driving rod, the incomplete bevel gear is not meshed with the lower bevel gear on the driving rod, thereby driving the driving rod and the detection device thereon to rotate around the head of the user for half a turn. The incomplete bevel gear is then in meshing transmission connection with the lower bevel gear on the driving rod. The incomplete bevel gear is not meshed with the upper bevel gear on the driving rod, so that the driving rod and the detection device thereon rotate around the head of the user in the opposite direction for half a turn, and cooperates with the camera and the millimeter-wave radar on the detection device, so that the camera can shoot and upload the face of a patient from different angles and carry out comparative detection through the processor. The millimeter-wave radar can detect the respiratory frequency and the heartbeat frequency of the user, which improves the detection effect of the device on face-to-face diagnosis of the user.

In addition, the pinion is in meshing transmission connection with the large gear at the bottom of the rotating rod. The transmission motor drives the pinion to rotate, thereby driving the large gear and the detection device thereon to rotate, and cooperate with the camera and the processor to be able to control the detection device of the device to rotate according to the position of the user, so that the millimeter-wave radar can detect the physical characteristics of the user such as the respiratory frequency and the heartbeat frequency at intervals.

BRIEF DESCRIPTION OF THE DRAWINGS

In order to explain the technical scheme of the embodiment of the present disclosure more clearly, the drawings of the embodiment will be briefly introduced hereinafter.

The drawings in the following description only relate to some embodiments of the present disclosure, rather than limit the present disclosure.

In the figures.

LIST OF REFERENCE NUMERALS

1. Base;
101. Guide rod; 102. Adjusting screw; 103. Adjusting motor;
2. Moving frame;
201. Bottom plate; 2011. Guide hole; 2012. Threaded hole; 202. Guide rail; 203. Limit plate;
3. Processor;
4. Mounting table;
401. Head supporting plate; 402. External slider;
5. Driving device;
501. Driving motor; 502. Incomplete bevel gear; 503. Driving rod; 5031. Upper bevel gear; 5032. Lower bevel gear;
6. Connecting frame;
601. Clamping groove;
7. Connecting arm body;
701. Guide groove; 702. Sliding rod; 7021. Limit post; 703. Elastic element; 704. Clamping block;
8. Detection device;
801. Supporting rod; 802. Camera; 803. Millimeter-wave radar; 804. Rotating rod;
9. Transmission device;
901. Transmission motor; 902. Pinion; 903. Large gear.

DETAILED DESCRIPTION OF THE EMBODIMENTS

In order to make the purpose, scheme and advantages of the technical scheme of the present disclosure clearer, the technical scheme of the embodiment of the present disclosure will be described clearly and completely in conjunction with the attached drawings of specific embodiments of the present disclosure hereinafter. Unless otherwise specified, the terms used herein have the ordinary meaning in the art. Like reference numerals in the drawings represent like parts.

Embodiment: refer to FIG. 1 to FIG. 10.

Figure 1:
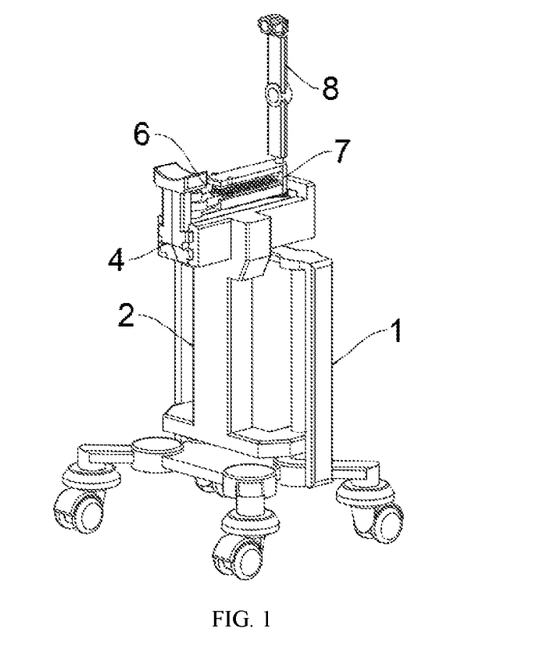
FIG. 1 shows a schematic diagram of a Traditional Chinese Medicine inspection device according to an embodiment of the present disclosure.
Figure 2:
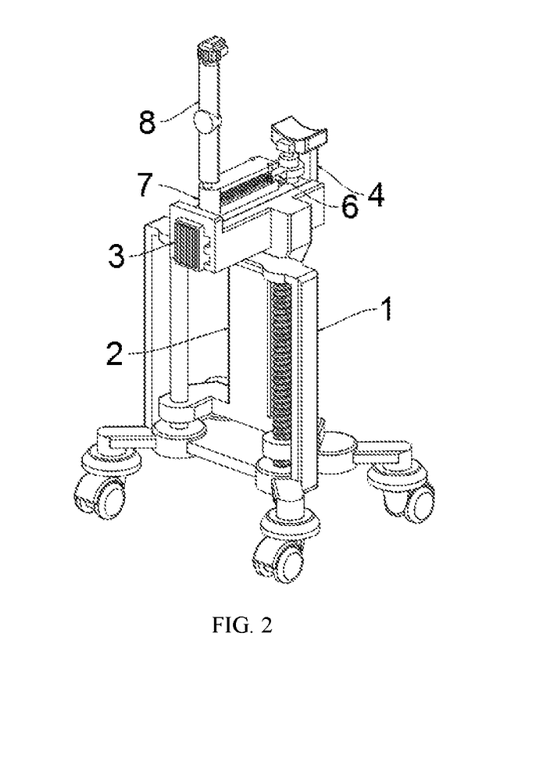
FIG. 2 shows an axial schematic diagram of the rear side of a Traditional Chinese Medicine inspection device according to the embodiment of the present disclosure.

The present disclosure provides a Traditional Chinese Medicine inspection device of a composite millimeter-wave radar, which comprises a base 1.

An adjusting screw 102 is rotatably installed at the left end of the base 1. A universal wheel is provided at the bottom end of the base 1. A moving frame 2 is threadedly installed at the top end of the base 1. A limit plate 203 is provided at the outer side of the top end of the moving frame 2. A processor 3 is installed at the rear end of the top surface of the moving frame 2. A remote transmission module is provided in the processor 3. A database is provided in the processor 3. A mounting table 4 is slidably installed at the top end of the moving frame 2. A head supporting plate 401 is provided at the top end of the front side of the mounting table 4. A driving device 5 is installed inside the mounting table 4. A connecting frame 6 is rotatably installed at the top end of the mounting table 4. The driving device 5 comprises a driving motor 501 and a driving rod 503. The driving motor 501 is fixedly installed at the inner bottom end of the mounting table 4. The driving rod 503 is fixedly installed at the left end of the connecting frame 6. The driving rod 503 is rotatably installed on the mounting table 4. A connecting arm body 7 is installed at the right end of the connecting frame 6. A clamping block 704 is slidably installed at the left bottom end of the connecting arm body 7. The clamping block 704 is clamped and installed at the top end of the connecting frame 6. A detection device 8 is rotatably installed at the right end of the connecting arm body 7. A transmission device 9 is installed at the bottom end of the connecting arm body 7. The detection device 8 comprises a supporting rod 801, a camera 802, a millimeter-wave radar 803 and a rotating rod 804. The camera 802 is installed at the middle section of the supporting rod 801. The millimeter-wave radar 803 is installed at the top end of the supporting rod 801. The rotating rod 804 is provided at the bottom end of the supporting rod 801. The transmission device 9 comprises a transmission motor 901, a pinion 902 and a large gear 903. The transmission motor 901 is fixedly installed at the right bottom end of the connecting arm body 7. The pinion 902 is installed on a transmission shaft of the transmission motor 901.

Figure 3:
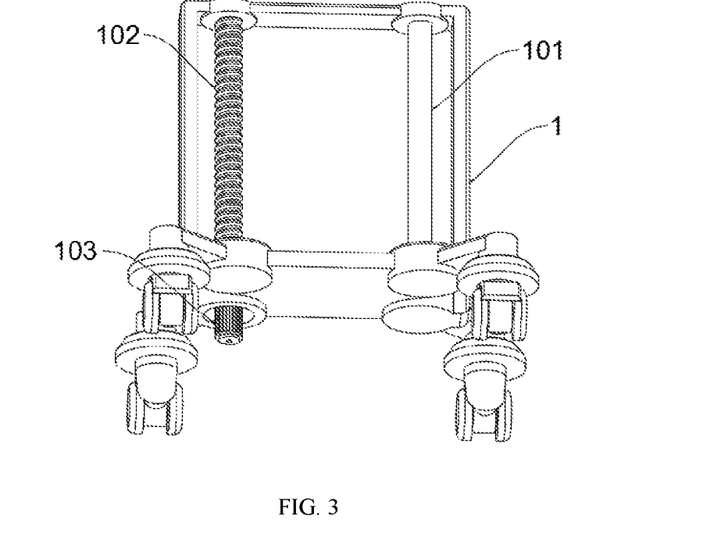
FIG. 3 shows a schematic diagram of a base of a Traditional Chinese Medicine inspection device according to an embodiment of the present disclosure.
Figure 4:
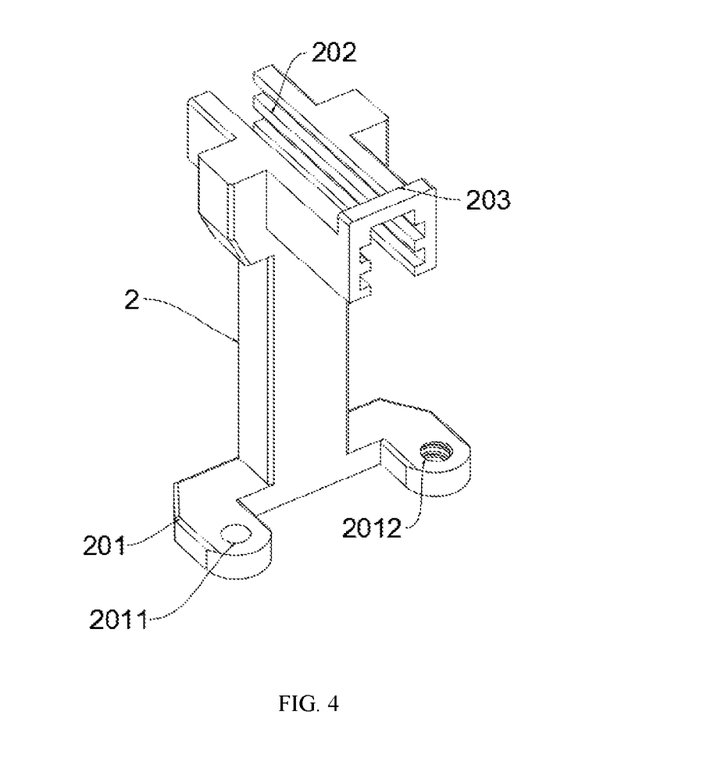
FIG. 4 shows a schematic diagram of a moving frame of a Traditional Chinese Medicine inspection device according to an embodiment of the present disclosure.
Figure 5:
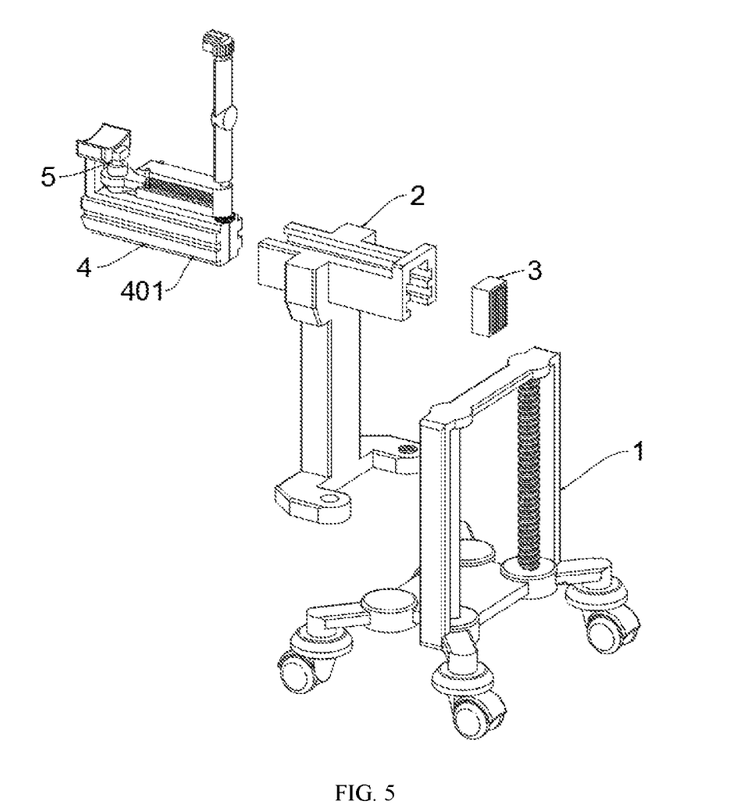
FIG. 5 shows a schematic diagram of the disassembly and assembly of a moving frame of a Traditional Chinese Medicine inspection device according to an embodiment of the present disclosure.
Figure 6:
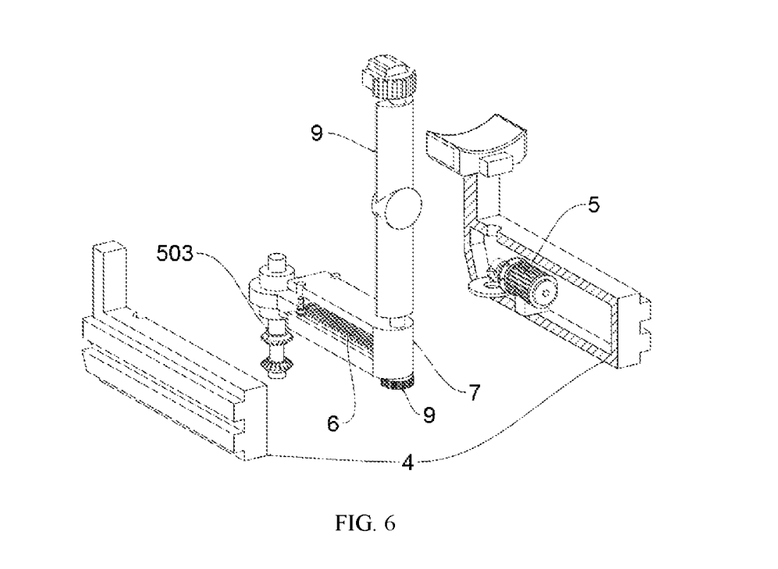
FIG. 6 shows a schematic diagram of the installation of a driving device of a Traditional Chinese Medicine inspection device according to an embodiment of the present disclosure.
Figure 7:
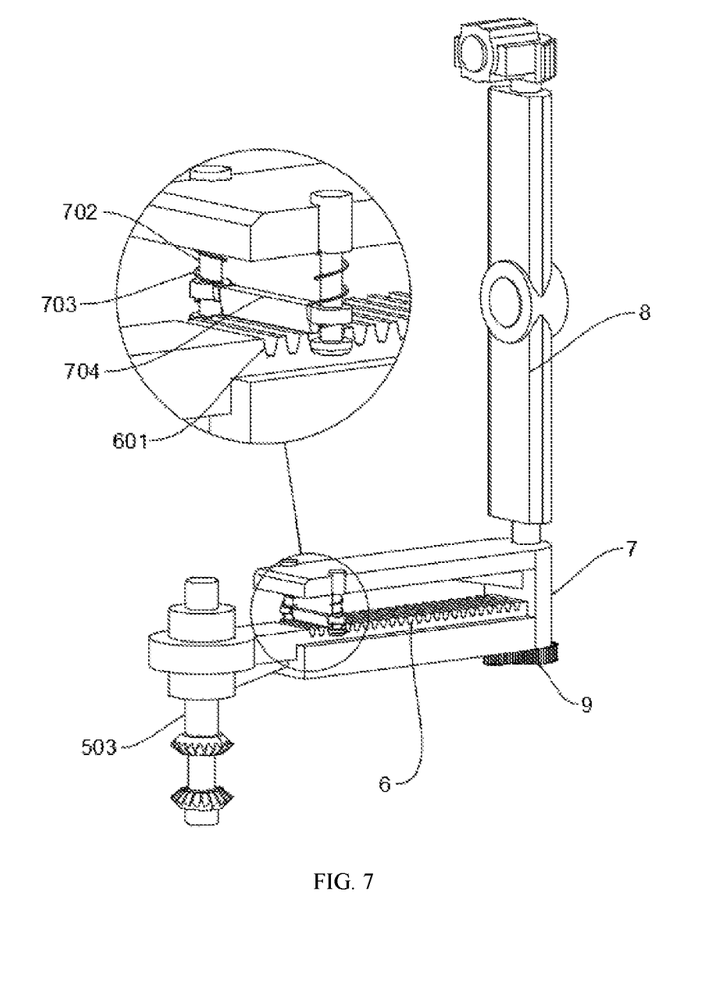
FIG. 7 shows a schematic diagram of the disassembly of a mounting table of a Traditional Chinese Medicine inspection device according to an embodiment of the present disclosure.
Figure 8:
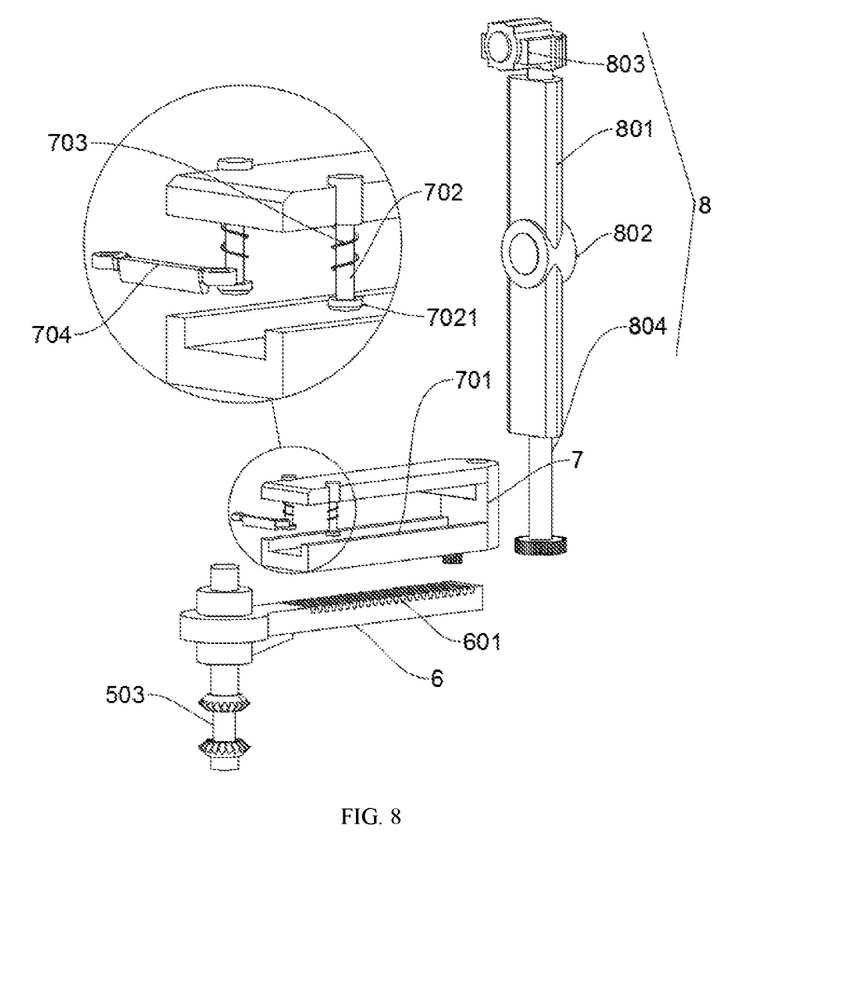
FIG. 8 shows a schematic diagram of a connecting arm body of a Traditional Chinese Medicine inspection device according to an embodiment of the present disclosure.

In addition, according to the embodiment of the present disclosure, as shown in FIGS. 3 and 4, a guide rod 101 is fixedly installed at the right end of the base 1. A bottom plate 201 is provided at the bottom end of the moving frame 2. A guide hole 2011 is provided at the right end of the bottom plate 201. The guide hole 2011 on the bottom plate 201 at the bottom end of the moving frame 2 is slidably installed on the guide rod 101 fixedly installed at the right end of the base 1. An adjusting motor 103 is fixedly installed at the left end of the base 1. The bottom end of the adjusting screw 102 is installed on the transmission shaft of the adjusting motor 103. A threaded hole 2012 is provided at the left end of the bottom plate 201 at the bottom end of the moving frame 2. The threaded hole 2012 on the bottom plate 201 at the bottom end of the moving frame 2 is threadedly installed on the adjusting screw 102 rotatably installed at the left end of the base 1. Specifically, the guide hole 2011 on the bottom plate 201 at the bottom end of the moving frame 2 is slidably installed on the guide rod 101 fixedly installed at the right end of the base 1. The threaded hole 2012 on the bottom plate 201 at the bottom end of the moving frame 2 is threadedly installed on the adjusting screw 102 rotatably installed at the left end of the base 1. The adjusting motor 103 drives the adjusting screw 102 to rotate, so that the moving frame 2 threadedly installed on the adjusting screw 102 and the head supporting plate 401 and the detecting device 8 thereon can be adjusted in height as required.

In addition, according to the embodiment of the present disclosure, as shown in FIGS. 5 to 8, two external sliders 402 are provided at the left side and the right side of the mounting table 4, respectively. A guide rail 202 is provided at the top end of the moving frame 2. The external sliders 402 at the left side and the right side of the mounting table 4 are slidably installed on the guide rail 202 provided at the top end of the moving frame 2. A guide groove 701 is provided at the top end of the connecting arm body 7. The right end of the connecting frame 6 is slidably installed on the guide groove 701 provided at the top end of the connecting arm body 7. The top surface of the connecting frame 6 is provided with clamping grooves 601 at equal intervals in an array. The bottom end of the clamping block 704 installed on the connecting arm body 7 is in a symmetrical italic structure with a narrow upper part and a wide lower part. The clamping block 704 on the connecting arm body 7 is clamped and installed on the clamping grooves 601 on the top surface of the connecting frame 6. Either end of the clamping block 704 slidably installed at the bottom end of the connecting arm body 7 is provided with a sliding hole, respectively. Two sliding rods 702 are fixedly installed on the left bottom surface of the connecting arm body 7. A limit post 7021 is provided at the bottom end of the sliding rod 702. The sliding holes at both ends of the clamping block 704 at the bottom end of the connecting arm body 7 are slidably installed on the sliding rod 702 fixedly installed on the left bottom surface of the connecting arm body 7, respectively. An elastic element 703 is sleeved and installed to either of the two sliding rods 702 on the left bottom surface of the connecting arm body 7, respectively. The bottom end of the elastic element 703 is in contact with the top end of the clamping block 704. Specifically, the external sliders 402 at the left side and the right side of the mounting table 4 are slidably installed on the guide rail 202 provided at the top end of the moving frame 2, so that the user can conveniently adjust the protruding position of the head supporting plate 401 on the mounting table 4 as required. The right end of the connecting frame 6 is slidably installed on the guide groove 701 provided at the top end of the connecting arm body 7. The sliding holes at the both ends of the clamping block 704 at the bottom end of the connecting arm body 7 are slidably installed on the sliding rod 702 fixedly installed on the left bottom surface of the connecting arm body 7, respectively. In cooperation with the elastic element 703 sleeved and installed on the sliding rod 702, the connecting frame 6 is pulled outwards, so that the clamping block 704 on the connecting arm body 7 is clamped and installed on different clamping grooves 601 on the top surface of the connecting frame 6. In this way, it is convenient to adjust the radius of the rotating arm of the detection device 8, so that the adjustable performance of the device is improved.

Figure 9:
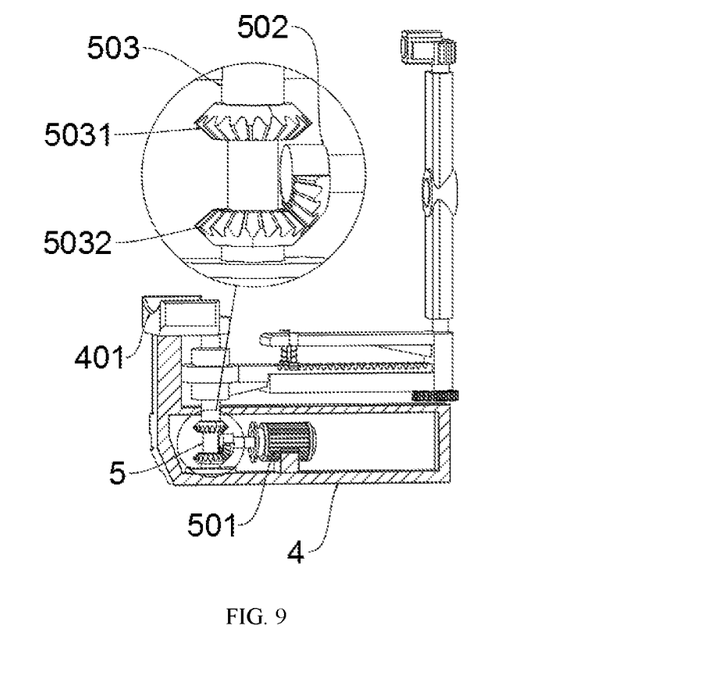
FIG. 9 shows a schematic diagram of the disassembly and assembly of a connecting arm body of a Traditional Chinese Medicine inspection device according to an embodiment of the present disclosure.
Figure 10:
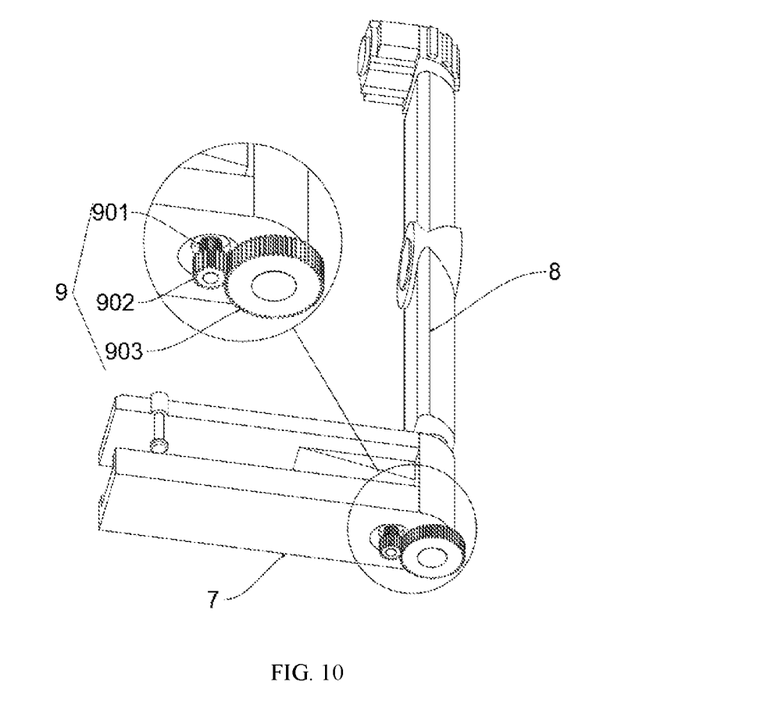
FIG. 10 shows a schematic diagram of a transmission device of a Traditional Chinese Medicine inspection device according to an embodiment of the present disclosure.

In addition, according to the embodiment of the present disclosure, as shown in FIG. 9, the driving device 5 further comprises an incomplete bevel gear 502, an upper bevel gear 5031 and a lower bevel gear 5032. The incomplete bevel gear 502 is installed on the transmission shaft of the driving motor 501. The upper bevel gear 5031 and the lower bevel gear 5032 are installed on the driving rod 503 oppositely. The upper bevel gear 5031 and the lower bevel gear 5032 are in meshing transmission connection with the incomplete bevel gear 502, respectively. Specifically, the user sticks his chin on the head supporting plate 401, so that the driving motor 501 drives the incomplete bevel gear 502 to rotate. When the incomplete bevel gear 502 is in meshing transmission connection with the upper bevel gear 5031 on the driving rod 503, the incomplete bevel gear 502 is not meshed with the lower bevel gear 5032 on the driving rod 503, thereby driving the driving rod 503 and the detection device 8 thereon to rotate around the head of the user for half a turn. The incomplete bevel gear 502 is then in meshing transmission connection with the lower bevel gear 5032 on the driving rod 503. The incomplete bevel gear 502 is not meshed with the upper bevel gear 5031 on the driving rod 503, so that the driving rod 503 and the detection device 8 thereon rotate around the head of the user in the opposite direction for half a turn, and cooperate with the camera 802 and the millimeter-wave radar 803 on the detection device 8, so that the camera 802 can shoot and upload the face of a patient from different angles and carry out comparative detection through the processor 3. The millimeter-wave radar 803 can detect the respiratory frequency and the heartbeat frequency of the user, which improves the detection effect of the device on face-to-face diagnosis of the user. As shown in FIG. 10, the rotating rod 804 on the detection device 8 is rotatably installed at the right end of the connecting arm body 7. The large gear 903 is fixedly installed at the bottom end of the rotating rod 804 on the detection device 8, and the pinion 902 is in meshing transmission connection with the large gear 903 at the bottom end of the rotating rod 804. Specifically, the pinion 902 is in meshing transmission connection with the large gear 903 at the bottom of the rotating rod 804. The transmission motor 901 drives the pinion 902 to rotate, thereby driving the large gear 903 and the detection device 8 thereon to rotate, and cooperate with the camera 802 and the processor 3 to be able to control the detection device 8 of the device to rotate according to the position of the user, so that the millimeter-wave radar 803 can detect the physical characteristics of the user such as the respiratory frequency and the heartbeat frequency at intervals.

The specific usage and function of the embodiment are as follows. In the present disclosure, the guide hole 2011 on the bottom plate 201 at the bottom end of the moving frame 2 is slidably installed on the guide rod 101 fixedly installed at the right end of the base 1. The threaded hole 2012 on the bottom plate 201 at the bottom end of the moving frame 2 is threadedly installed on the adjusting screw 102 rotatably installed at the left end of the base 1. The adjusting motor 103 drives the adjusting screw 102 to rotate, so that the moving frame 2 threadedly installed on the adjusting screw 102 and the head supporting plate 401 and the detecting device 8 thereon can be adjusted in height as required. The external sliders 402 at the left side and the right side of the mounting table 4 are slidably installed on the guide rail 202 provided at the top end of the moving frame 2, so that the user can conveniently adjust the protruding position of the head supporting plate 401 on the mounting table 4 as required. The right end of the connecting frame 6 is slidably installed on the guide groove 701 provided at the top end of the connecting arm body 7. The sliding holes at the both ends of the clamping block 704 at the bottom end of the connecting arm body 7 are slidably installed on the sliding rod 702 fixedly installed on the left bottom surface of the connecting arm body 7, respectively. In cooperation with the elastic element 703 sleeved and installed on the sliding rod 702, the connecting frame 6 is pulled outwards, so that the clamping block 704 on the connecting arm body 7 is clamped and installed on different clamping grooves 601 on the top surface of the connecting frame 6. In this way, it is convenient to adjust the radius of the rotating arm of the detection device 8, so that the adjustable performance of the device is improved. The user sticks his chin on the head supporting plate 401, so that the driving motor 501 drives the incomplete bevel gear 502 to rotate. When the incomplete bevel gear 502 is in meshing transmission connection with the upper bevel gear 5031 on the driving rod 503, the incomplete bevel gear 502 is not meshed with the lower bevel gear 5032 on the driving rod 503, thereby driving the driving rod 503 and the detection device 8 thereon to rotate around the head of the user for half a turn. The incomplete bevel gear 502 is then in meshing transmission connection with the lower bevel gear 5032 on the driving rod 503. The incomplete bevel gear 502 is not meshed with the upper bevel gear 5031 on the driving rod 503, so that the driving rod 503 and the detection device 8 thereon rotate around the head of the user in the opposite direction for half a turn, and cooperate with the camera 802 and the millimeter-wave radar 803 on the detection device 8, so that the camera 802 can shoot and upload the face of a patient from different angles and carry out comparative detection through the processor 3. The millimeter-wave radar 803 can detect the respiratory frequency and the heartbeat frequency of the user, which improves the detection effect of the device on face-to-face diagnosis of the user. The pinion 902 is in meshing transmission connection with the large gear 903 at the bottom of the rotating rod 804. The transmission motor 901 drives the pinion 902 to rotate, thereby driving the large gear 903 and the detection device 8 thereon to rotate, and cooperate with the camera 802 and the processor 3 to be able to control the detection device 8 of the device to rotate according to the position of the user, so that the millimeter-wave radar 803 can detect the physical characteristics of the user such as the respiratory frequency and the heartbeat frequency at intervals.

Finally, it should be noted that the present disclosure usually takes one/a pair of components as an example when describing the positions of various components and the mating relationship between them. However, it should be understood by those skilled in the art that such positions, mating relationships, etc. are also applicable to other components/other paired components.

The above is only an exemplary embodiment of the present disclosure, rather than limit the scope of protection of the present disclosure. The scope of protection of the present disclosure is determined by the appended claims.

What is claimed is:

1. A medicine inspection device of a composite millimeter-wave radar comprising:
   a base;
   an adjusting screw is rotatably installed at a left end of the base, a universal wheel is provided at a bottom end of the base, a moving frame is threadedly installed at a top end of the base, a limit plate is provided at an outer side of a top end of the moving frame, a processor is installed at a rear end of a top surface of the moving frame, a remote transmission module is provided in the processor, a database is provided in the processor, a mounting table is slidably installed at the top end of the moving frame, a head supporting plate is provided at a top portion of a front side of the mounting table, a driving device is installed inside the mounting table, and a connecting frame is rotatably installed at a top end of the mounting table;
   the driving device comprises a driving motor and a driving rod, the driving motor is fixedly installed at an inner bottom end of the mounting table, the driving rod is fixedly installed at a left end of the connecting frame, and the driving rod is rotatably installed on the mounting table; a connecting arm body is installed at a right end of the connecting frame; a clamping block is slidably installed at a left side of a bottom end of the connecting arm body, the clamping block is clamped and installed at a top end of the connecting frame, a detection device is rotatably installed at a right end of the connecting arm body, a transmission device is installed at the bottom end of the connecting arm body, the detection device comprises a supporting rod, a camera, a millimeter-wave radar and a rotating rod, the camera is installed at a middle section of the supporting rod, the millimeter-wave radar is installed at a top end of the supporting rod, and the rotating rod is provided at a bottom end of the supporting rod; the transmission device comprises a transmission motor, a pinion and a gear, the transmission motor is fixedly installed at a right side of the bottom end of the connecting arm body, and the pinion is installed on a transmission shaft of the transmission motor.

2. The medicine inspection device of claim 1, wherein a guide rod is fixedly installed at a right end of the base, a bottom plate is provided at a bottom end of the moving frame, a guide hole is provided at a right end of the bottom plate, and the guide hole on the bottom plate at the bottom end of the moving frame is slidably installed on the guide rod fixedly installed at the right end of the base.

3. The medicine inspection device of claim 2, wherein an adjusting motor is fixedly installed at the left end of the base, a bottom end of the adjusting screw is installed on a transmission shaft of the adjusting motor, a threaded hole is provided at a left end of the bottom plate at the bottom end of the moving frame, and the threaded hole on the bottom plate at the bottom end of the moving frame is threadedly installed on the adjusting screw rotatably installed at the left end of the base.

4. The medicine inspection device of claim 1, wherein two external sliders are provided at a left side and a right side of the mounting table, respectively, a guide rail is provided at the top end of the moving frame, and the external sliders at the left side and the right side of the mounting table are slidably installed on the guide rail provided at the top end of the moving frame.

5. The medicine inspection device of claim 1, wherein a guide groove is provided at a top end of the connecting arm body, and the right end of the connecting frame is slidably installed on the guide groove provided at the top end of the connecting arm body.

6. The medicine inspection device of claim 1, wherein a top surface of the connecting frame is provided with clamping grooves at equal intervals in an array, a bottom end of the clamping block installed on the connecting arm body is in a symmetrical italic structure with a narrow upper part and a wide lower part, and the clamping block on the connecting arm body is clamped and installed on the clamping grooves on the top surface of the connecting frame.

7. The medicine inspection device of claim 1, wherein each end of the clamping block slidably installed at the bottom end of the connecting arm body is provided with a sliding hole, respectively, two sliding rods are fixedly installed on a left bottom surface of the connecting arm body, a limit post is provided at the bottom end of each sliding rod, and the sliding holes at both ends of the clamping block at the bottom end of the connecting arm body are slidably installed on the sliding rods fixedly installed on the left bottom surface of the connecting arm body, respectively.

8. The medicine inspection device of claim 7, wherein an elastic element is sleeved and installed to either of the two sliding rods on the left bottom surface of the connecting arm body, respectively, and a bottom end of the elastic element is in contact with a top end of the clamping block.

9. The medicine inspection device of claim 1, wherein the driving device further comprises an incomplete bevel gear, an upper bevel gear and a lower bevel gear, the incomplete bevel gear is installed on a transmission shaft of the driving motor, the upper bevel gear and the lower bevel gear are installed on the driving rod oppositely, and the upper bevel gear and the lower bevel gear are in meshing transmission connection with the incomplete bevel gear, respectively.

10. The medicine inspection device of claim 1, wherein the rotating rod on the detection device is rotatably installed at the right end of the connecting arm body, the gear is fixedly installed at a bottom end of the rotating rod on the detection device, and the pinion is in meshing transmission connection with the gear at the bottom end of the rotating rod.

* * * * *